(12) United States Patent
Shimosoyama et al.

(10) Patent No.: US 9,180,073 B2
(45) Date of Patent: Nov. 10, 2015

(54) SILICONE IMPRESSION MATERIAL HAVING HIGH HYDROPHILICITY

(71) Applicant: SHOFU INC., Kyoto (JP)

(72) Inventors: Shun Shimosoyama, Kyoto (JP); Toshio Kitamura, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 43 days.

(21) Appl. No.: 13/762,910

(22) Filed: Feb. 8, 2013

(65) Prior Publication Data

US 2013/0210958 A1    Aug. 15, 2013

(30) Foreign Application Priority Data

Feb. 10, 2012    (JP) .................. 2012-026787

(51) Int. Cl.
*A61K 6/10*    (2006.01)
(52) U.S. Cl.
CPC ........................ *A61K 6/10* (2013.01)
(58) Field of Classification Search
USPC .......... 523/109; 528/15, 31; 433/214
See application file for complete search history.

(56) References Cited

U.S. PATENT DOCUMENTS

| | | | |
|---|---|---|---|
| 4,782,101 A | 11/1988 | Waller et al. | |
| 4,806,575 A | 2/1989 | Waller et al. | |
| 5,907,002 A | 5/1999 | Kamohara et al. | |
| 6,762,242 B1 * | 7/2004 | Torto et al. | 524/588 |
| 6,861,457 B2 * | 3/2005 | Kamohara | 523/109 |
| 2004/0152858 A1 | 8/2004 | Kamohara et al. | |
| 2010/0184881 A1 | 7/2010 | Zech et al. | |
| 2011/0281237 A1 * | 11/2011 | Riedel et al. | 433/214 |

FOREIGN PATENT DOCUMENTS

| | | |
|---|---|---|
| EP | 0231420 | 8/1987 |
| EP | 1 290 998 | 3/2003 |
| GB | 2 337 524 | 11/1999 |
| JP | 62-252706 | 11/1987 |
| JP | 63-130510 | 6/1988 |
| JP | 05-271545 | 10/1993 |
| JP | 2004-182823 | 7/2004 |
| JP | 4090536 | 3/2008 |
| JP | 4154576 | 7/2008 |
| JP | 2009-203196 | 9/2009 |
| JP | 2011-506612 | 3/2011 |
| WO | 2009/079534 | 6/2009 |

OTHER PUBLICATIONS

European Search Report dated Feb. 20, 2014.
JP 10-072307, Mar. 17, 1998 (English abstract, corresponds to JP4090536 & US5907002, discussed in specification).

* cited by examiner

*Primary Examiner* — Tae H Yoon
(74) *Attorney, Agent, or Firm* — Rankin, Hill & Clark LLP

(57) ABSTRACT

Provided is a silicone impression material with high hydrophilicity that exhibits instantaneous hydrophilicity before being cured, that exhibits high hydrophilicity after being cured, that has preferable properties for a dental impression material, and that has good preservation stability. A sorbitan fatty acid ester based surfactant and a nonionic surfactant composed of polyether modified silicone are used in combination as a hydrophilizing agent not containing a siloxane polymer and a hydrophilizing agent containing a siloxane polymer, respectively.

4 Claims, 10 Drawing Sheets

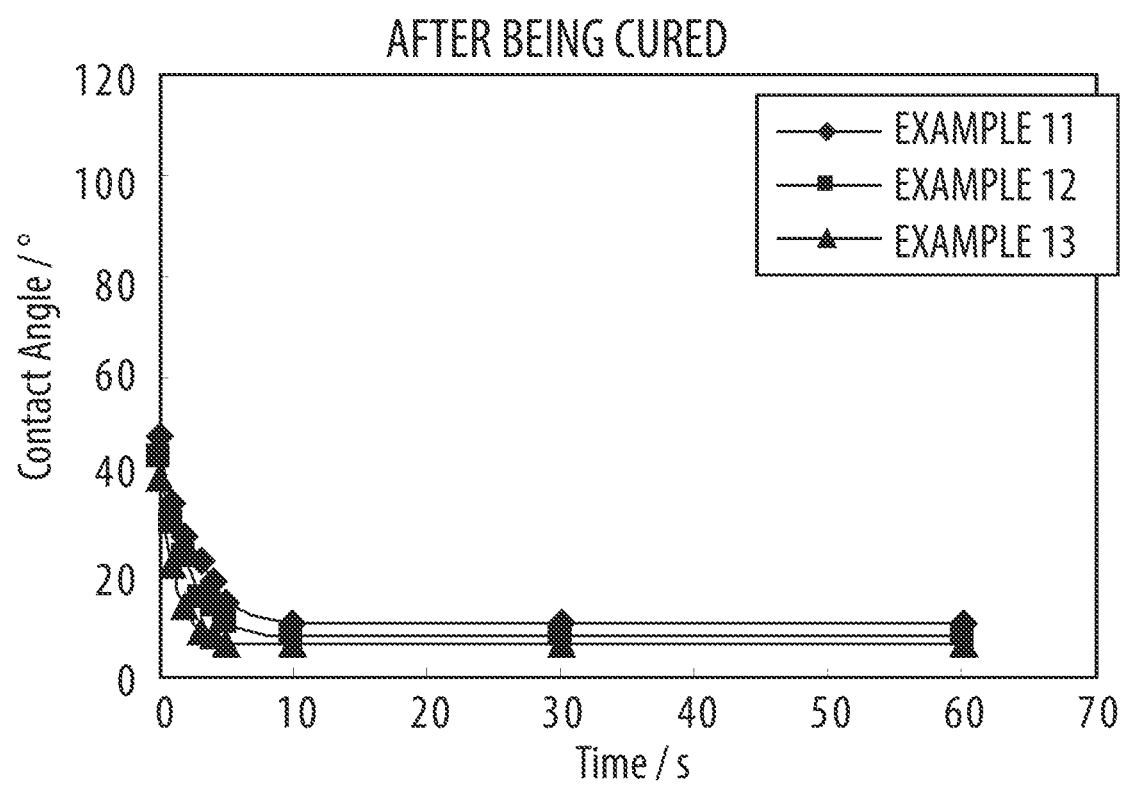

SILICONE IMPRESSION MATERIAL HAVING HIGH HYDROPHILICITY

BACKGROUND OF THE INVENTION

1. Field of the Invention

The present invention relates to a silicone impression material having high hydrophilicity, and more particularly to a silicone impression material of an addition reaction type having high hydrophilicity.

2. Background Art

Impression materials have been used since long before in a variety of oral treatment to assess oral conditions. Impression materials are essential to fabricate dental prosthetic appliances in various situations of dental treatment, particularly when a tooth substance is lost because of dental caries or an oral environment is otherwise diseased and thus needs adjustment, and in case of implant dentistry treatment or esthetic dentistry treatment which has become widespread in recent years.

In general, impression materials used to assess oral conditions are pasty viscous material, and cured by a variety of curing mechanisms to change into a gummy elastic material. In clinical situations, a pasty impression material is pressed onto a location, the impression of which is to be taken. After the impression material is held for a certain period, it is checked whether the impression material has changed into a gummy elastic material, and then the cured impression material is taken out of the oral cavity.

While various types of impression materials have been developed so far, alginate impression materials, agar impression materials, and silicone impression materials are mainly used today.

Among the alginate impression materials, alginate impression materials of a powder type containing alginate powder and cured when mixed with water were commonly used. In recent years, however, alginate impression materials of a paste-paste type having good preservation stability have been increasingly used. In Japan, in particular, the alginate impression materials are often used in combinations with the agar impression materials, and known as common impression materials for health insurance treatment.

The agar impression materials containing thermoplastic gel at high temperature is in the sol state and is galated to be cured as the temperature lowers. In Japan, in particular, the agar impression materials are often used in combinations with the alginate impression materials, and known as common impression materials for health insurance treatment.

The silicone impression materials contain two types of pastes, namely a base paste and a catalyst paste, which are kneaded with each other to be cured into a gummy elastic material. The silicone impression materials are roughly divided into a condensation type and an addition type depending on the curing mechanism. In recent years, the silicone impression materials of the addition type have been mainly used from the viewpoint of their high dimensional accuracy and the safety of their composition to human bodies.

The silicone impression materials of the addition type hardly change in dimensions after being cured, and there is almost no need to consider their changes in dimensions in an environment around room temperature. In this point, the silicone impression materials of the addition type are superior to the alginate impression materials and the agar impression materials. However, the silicone impression materials contain a siloxane polymer that is generally hydrophobic, and therefore are disadvantageously incompatible with wet tissues compared to the alginate impression materials and the agar impression materials. Normally, the oral cavity is in a wet environment, and it is difficult to completely dry a location, the impression of which is to be taken. If tissues in the oral cavity are completely dried, the oral cavity is no longer in its usual state, and is not suitable for impression sampling. A plaster modeling material is injected into the impression material taken out of the oral cavity. However, the silicone impression materials of the addition type are also less compatible with the plaster modeling material than the alginate impression materials and the agar impression materials.

In order to address such drawbacks, a variety of attempts have made to add hydrophilicity to the silicone impression materials, such as by adding a surfactant, by compositing a material having hydrophilicity, and by synthesizing a siloxane polymer having a hydrophilic group, as taught in the patent documents mentioned below.

Japanese Patent Application Publication No. 63-130510 (JP63-130510A) describes an example of a silicone impression material according to the related art. The publication discloses that hydrophilicity of the dental impression material can be enhanced by including a surfactant selected from polyol fatty acid ester based and ethoxylated ester based surfactants in a dental impression material containing a vinyl polydimethylsiloxane, a hydro-polydimethylsiloxane, a silica filler, a cyclic vinyl siloxane, a chloroplatinic acid complex, platinum black, and a plasticizer.

Japanese Patent No. 4090536 discloses a silicone impression material for dental impression that is highly elastic with large elastic strain and small permanent strain, that does not drip or tear during impression taking, and that is highly wettable with water. The silicone impression material disclosed therein is obtained by adding respective specific amounts of impalpable silica powder, a nonionic surfactant, and a methylphenyl polysiloxane to a silicone impression material of an addition polymerization type containing an organopolysiloxane having at least two aliphatic unsaturated hydrocarbon groups in a molecule, an organohydrogen polysiloxane having at least three hydrogen atoms directly bonded to a silicon atom in a molecule, a silicone-soluble platinum compound, and an inorganic filler.

Japanese Patent Application Publication No. 62-252706 (JP62-252706A) discloses an organopolysiloxane composition containing a silicone-polyether compound having a hydrophobic silicone portion and at least one hydrophilic polyether portion, to express hydrophilicity to wet tissues.

Japanese Patent Application Publication No. 2011-506612 (JP2011-506612A) discloses a dental impression material containing a curable organopolysiloxane polymer, a cross-linking agent compound capable of cross-linking the organopolysiloxane polymer, a catalyst capable of catalyzing the cross-linking reaction, a surfactant, and an F-containing compound, to express hydrophilicity both before and after being cured.

Japanese Patent No. 4154576 discloses combining a base polymer containing a curable organopolysiloxane containing 5 mol % or more of diphenyl siloxane units or 10 mol % or more of methylphenyl siloxane units with a polyether to obtain a highly hydrophilic curable material having a contact angle of 70° or less, in particular 65° or less, based on JIS R3257. Japanese Patent No. 4154576 further discloses that the obtained highly hydrophilic curable material is cured well even after a long period of storage because the polyether is not easily separated from the compound or the curable material, thereby suppressing variations in wettability with a water-based paint or in impression performance and showing superior hardening property.

Although the impression material according to Japanese Patent Application Publication No. 63-130510 (JP63-130510A) exhibits high hydrophilicity before being cured, the impression material does not reproduce a plaster model well, and the hydrophilizing agent adversely affects the physical properties for a dental impression material. Therefore, the impression material may not maintain desirable physical properties for a dental impression material, or has poor preservation stability.

Although the impression material according to Japanese Patent No. 4090536 exhibits high hydrophilicity before being cured, the impression material does not have high hydrophilicity after being cured, and may not reproduce details when plaster is injected.

Although the impression material according to Japanese Patent Application Publication No. 62-252706 (JP62-252706A) provides sufficient hydrophilicity after being cured, the impression material does not provide sufficient hydrophilicity before being cured, and may not produce details during impression sampling.

The impression material according to Japanese Patent Application Publication No. 2011-506612 (JP2011-506612A) is slow in expressing hydrophilicity, and may take time to become compatible with wet organisms in the oral cavity.

The impression material according to Japanese Patent No. 4154576 is slow in expressing hydrophilicity, and may take time to become compatible with wet organisms in the oral cavity.

The dental impression materials according to the related art taught in the patent documents mentioned above do not instantly express high hydrophilicity in the oral cavity before being cured, and do not exhibit high hydrophilicity when plaster is poured after being cured. Therefore, an impression that reproduces details of the oral cavity well may not be obtained immediately using the dental impression materials according to the related art.

SUMMARY OF THE INVENTION

An object of the present invention is to provide a silicone impression material of the addition reaction type that exhibits high hydrophilicity before and after being cured, that instantly expresses hydrophilicity to wet organisms, that maintains preferable properties for a dental impression material, and that has good preservation stability.

In order to address the foregoing issues, the inventors made an earnest study to find that a sorbitan fatty acid ester and a polyether modified silicone did not adversely affect each other's physical properties. The inventors also found that the sorbitan fatty acid ester and the polyether modified silicone did not adversely affect the properties and the preservation stability of a dental impression material. Based on such findings, the inventors made a research on use of a nonionic surfactant composed of polyether modified silicone serving as a hydrophilizing agent containing a siloxane polymer in combination with use of a sorbitan fatty acid ester based surfactant serving as a hydrophilizing agent not containing a siloxane polymer. As a result, it was found that the resulting silicone impression material expressed instantaneous hydrophilicity before being cured, expressed high hydrophilicity after being cured, had preferable properties for a dental impression material, and had good preservation stability. The present invention has been made based on the above findings.

The present invention improves a silicone impression material including:

organopolysiloxanes having at least two unsaturated groups in a molecule, as a component (1);

organohydrogen polysiloxanes having at least two SiH groups in a molecule, as a component (2);

a filler as a component (3); and a platinum catalyst as a component (4).

The silicone impression material according to the present invention also includes, as a hydrophilizing agent:

a sorbitan fatty acid ester based surfactant as a component (a); and a nonionic surfactant composed of polyether modified silicone, as a component (b).

The silicone impression material according to the present invention exhibits instantaneous hydrophilicity before being cured, exhibits high hydrophilicity after being cured, has preferable properties for a dental impression material, and has good preservation stability.

In a specific silicone impression material, in the total composition of the silicone impression material, the organopolysiloxanes as the component (1) account for 20 to 70 wt %;

the organohydrogen polysiloxanes as the component (2) account for 3 to 15 wt %;

the filler as the component (3) accounts for 20 to 70 wt %;

the platinum catalyst as the component (4) accounts for 0.01 to 0.5 wt %;

the sorbitan fatty acid ester based surfactant as the component (a) accounts for 0.25 to 6 wt %; and the nonionic surfactant as the component (b) accounts for 0.25 to 15 wt %.

The silicone impression material configured to include the components in such amounts is promoted to exhibit higher instantaneous hydrophilicity before being cured, exhibit higher hydrophilicity after being cured, have more preferable properties for a dental impression material, and have better preservation stability. It is a matter of course that the silicone impression material according to the present invention may include contents outside the numerical ranges described above, and the silicone impression material according to the present invention including contents outside the numerical ranges described above also exhibits instantaneous hydrophilicity before being cured, exhibits high hydrophilicity after being cured, has preferable properties for a dental impression material, and has good preservation stability.

Preferably, the sorbitan fatty acid ester based surfactant as the component (a) has an HLB of 6.0 to 10.0. The term "HLB" used herein indicates a numerical representation of the balance in intensity between the hydrophilicity and the hydrophobicity, and is given by a formula HLB=(total formula weight of hydrophilic portions/total molecular weight)×100÷5. According to the formula, a material having no hydrophilic groups has an HLB of 0, and a material having only hydrophilic groups has an HLB of 20. Thus, the HLB is in the range of 0 to 20. A smaller HLB value means higher hydrophobicity, and a larger HLB value means higher hydrophilicity. When the sorbitan fatty acid ester based surfactant has an HLB of 6.0 to 10.0, the hydrophilicity of the silicone impression material is not very low, and the silicone impression material has small initial permanent strain and elastic strain. When the sorbitan fatty acid ester based surfactant as the component (a) has an HLB of 7.0 to 10.0, in particular, the sorbitan fatty acid ester based surfactant advantageously has higher hydrophilicity. When the content of the sorbitan fatty acid ester based surfactant is in the range of 2 to 4 wt %, the silicone impression material advantageously expresses hydrophilicity more immediately after water drips, both before and after being cured, and has smaller permanent strain, larger elastic strain, and better preservation stability.

Preferably, the nonionic surfactant as the component (b) is a compound of the following formula: <Formula 1>

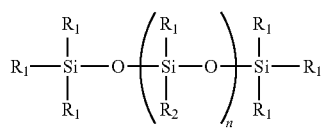
[1]

wherein $R_1$ is an optionally substituted alkyl or aryl group; $R_1$'s are the same or different; n is an integer of 1 or more; $R_2$ is a substituent having an alkoxy group and composed of a main chain containing an ether bond when n=1; $R_2$ is a substituent having an alkoxy group and composed of a main chain containing an optionally substituted alkyl group, aryl group, or ether bond when n≥2; at least one of $R_2$'s is a substituent having an alkoxy group and composed of a main chain containing an ether bond when n≥2; and combinations of $R_1$ and $R_2$ in a monomer unit are the same or different for each monomer unit when n≥2. When such a nonionic surfactant composed of polyether modified silicone as the component (b) is used, high hydrophilicity may be maintained compared to a case where different nonionic surfactants composed of polyether modified silicone are used.

Preferably, n≤100. When n is more than 100, it may be difficult for the silicone impression material to express hydrophilicity, or the physical properties of the silicone impression material after being cured may be adversely affected.

Preferably, the polyether modified silicone as the component (b) has an HLB of 5.0 to 18.0. When the polyether modified silicone having an HLB of 5.0 to 18.0 is used, a reduction in hydrophilicity may be sufficiently suppressed. When the HLB is less than 5.0, the hydrophilicity is low compared to a case where the HLB is in the range of 5.0 to 18.0. When the polyether modified silicone as the component (b) has an HLB of 10.0 to 18.0, in particular, high hydrophilicity is advantageously expressed compared to a case where the HLB is outside the range of 10.0 to 18.0.

Preferably, the filler as the component (3) has a maximum grain size of not more than 50 μm. When the maximum grain size of the filler is more than 50 μm, elastic strain may be reduced, permanent strain may be increased, and/or tearing strength may be reduced.

When seen differently, preferably, a content ratio of the sorbitan fatty acid ester based surfactant as the component (a) and the nonionic surfactant as the component (b) is 1:1 to 1:2. When the content ratio is in this range, the silicone impression material expresses hydrophilicity immediately after water drips, both before and after being cured, and continuously exhibits high hydrophilicity thereafter. The initial physical properties of the silicone impression material are desirable with small permanent strain and large elastic strain. The silicone impression material is sharply cured, and has good preservation stability. When a content ratio of the sorbitan fatty acid ester based surfactant as the component (a) and the nonionic surfactant as the component (b) is 1:1.5 to 1:1.8, in particular, it is possible to prevent a reduction in hydrophilicity, poor initial physical properties, and an occurrence of a problem that hydrophilicity is not immediately expressed.

A more preferable specific example of the present invention meets the following numerical ranges:
the organopolysiloxanes as the component (1) account for 37.9 to 50.9 wt %;
the organohydrogen polysiloxanes as the component (2) account for 8 wt %;
the filler as the component (3) accounts for 36 wt %;
the platinum catalyst as the component (4) accounts for 0.1 wt %;
the sorbitan fatty acid ester based surfactant as the component (a) accounts for 0.25 to 6 wt %; and
the nonionic surfactant as the component (b) accounts for 0.25 to 12 wt %.

The silicone impression material that meets such numerical ranges expresses higher instantaneous hydrophilicity before and after being cured in addition to the effects described above.

When the numerical ranges described above are used, the organopolysiloxanes as the component (1) may be α-ω divinyl polysiloxane, and the organohydrogen polysiloxanes as the component (2) may be dimethyl hydrogen polysiloxane. In this case, the sorbitan fatty acid ester based surfactant as the component (a) may be sorbitan monooleate, polyoxyethylene sorbitan oleate, sorbitan laurate, sorbitan caprylate, or polyoxyethylene sorbitan monostearate. Preferably, the nonionic surfactant as the component (b) is a side chain type or a terminal type. The silicone impression material that meets the combination of conditions expresses better instantaneous hydrophilicity before and after being cured in addition to the effects described above.

A still more preferable specific example of the present invention meets the following numerical ranges:
the organopolysiloxanes as the component (1) account for 44.9 to 50.9 wt %;
the organohydrogen polysiloxanes as the component (2) account for 8 wt %;
the filler as the component (3) accounts for 36 wt %;
the platinum catalyst as the component (4) accounts for 0.1 wt %;
the sorbitan fatty acid ester based surfactant as the component (a) accounts for 2 to 4 wt %; and
the nonionic surfactant as the component (b) accounts for 3 to 7 wt %.

The silicone impression material that meets such numerical ranges expresses higher instantaneous hydrophilicity before and after being cured and better initial physical properties in addition to the effects described above.

When the numerical ranges described above are used, the organopolysiloxanes as the component (1) may be α-ω divinyl polysiloxane, and the organohydrogen polysiloxanes as the component (2) may be dimethyl hydrogen polysiloxane. The sorbitan fatty acid ester based surfactant as the component (a) may be polyoxyethylene sorbitan monostearate or sorbitan laurate. The nonionic surfactant as the component (b) may be a side chain type. The silicone impression material that meets the combination of conditions expresses better instantaneous hydrophilicity before and after being cured and better initial physical properties in addition to the effects described above.

BRIEF DESCRIPTION OF THE DRAWINGS

FIG. 10 is a graph showing temporal variations in contact angle of the silicone impression materials according to Examples 11 to 13 after being cured.

DESCRIPTION OF THE PREFERRED EMBODIMENTS

Figure 1:
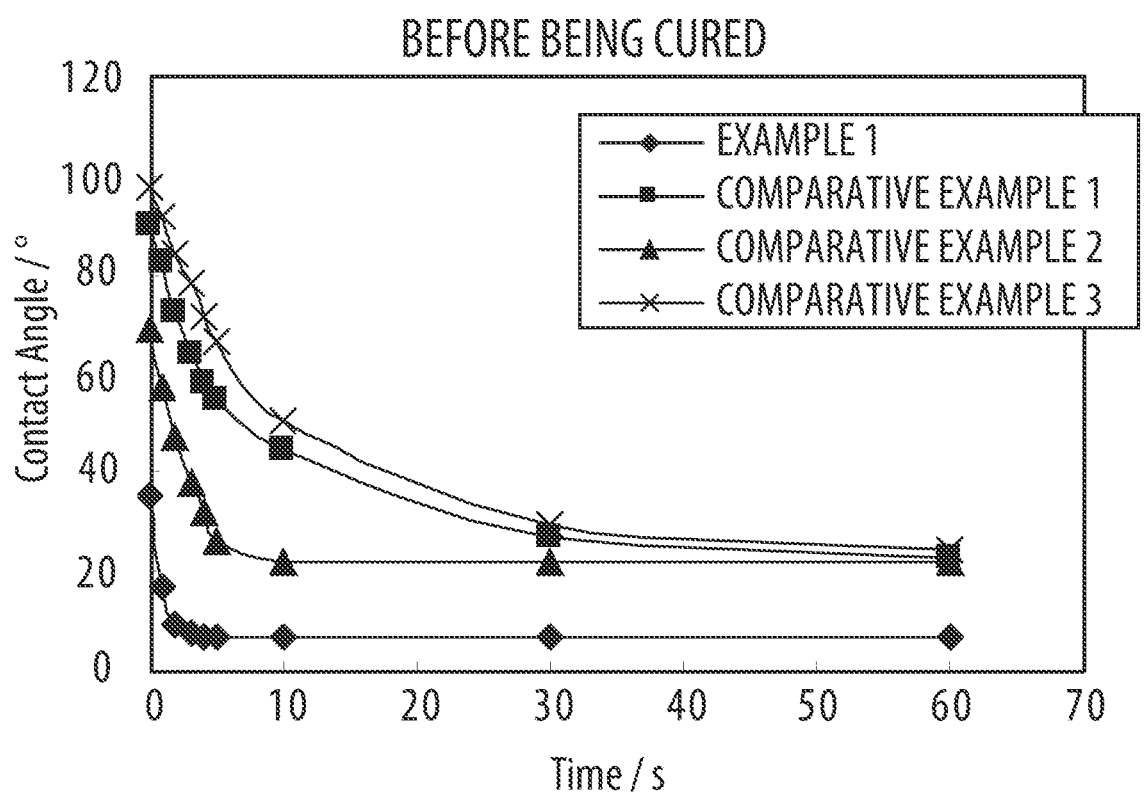
FIG. 1 is a graph showing temporal variations in contact angle of silicone impression materials according to Example 1 and Comparative Examples 1 to 3 before being cured.

The organopolysiloxanes having at least two unsaturated groups in a molecule, as the component (1), used in the silicone impression material according to the present invention is an organopolysiloxane having at least two organic groups bonded to at least one organic group having an ethylenically unsaturated double bond. The organic group having an ethylenically unsaturated double bond is located on any monomer unit of the organopolysiloxane, and preferably located on, or at least near, a terminal monomer unit of a polymer chain of the organopolysiloxane. Particularly preferably, at least two of the organic groups having an ethylenically unsaturated double bond are located at the α,ω position, that is, at the terminal of the polymer chain. Use of such organopolysiloxanes facilitates formation of a three-dimensional network structure to express high rubber hardness. The organopolysiloxane is represented by the general formula [2]: <Formula 2>

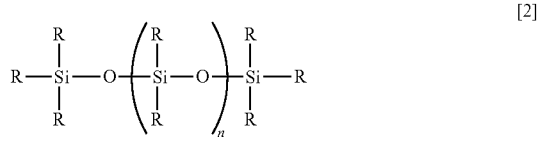

[2]

In the formula, R is an optionally substituted alkyl, aryl, or alkenyl group, and R's may be the same or different. n is an integer of 1 or more. R's in each monomer unit may be the same or different. R's in different monomer units may be the same or different.

Preferably, n≤100. When n is larger than 100, the viscosity may be increased to adversely affect the operability.

The symbol "R" used herein represents an unsubstituted or substituted monovalent hydrocarbon group, which may be a straight-chain group, or may be a straight-chain, branched-chain, or cyclic group if there are more than three carbon atoms. In general, R may include any type of substituent that does not hinder a curing reaction.

The term "hinder" used herein means that the substituent adversely affects the curing reaction.

The term "adversely" used herein means that the properties of the cured product are negatively changed against its intended purpose of use.

The amount of the organopolysiloxanes having at least two unsaturated groups in a molecule as the component (1) is preferably in the range of 20 to 70 wt % based on the total amount of the silicone impression material.

The organohydrogen polysiloxanes having at least two SiH groups in a molecule, as the component (2), are subjected to a hydrosilylation addition reaction with the organopolysiloxane containing unsaturated hydrocarbon as the component (1) to act as a cross-linking agent capable of curing the silicone impression material. The component (2) is a compound represented by the general formula [3]: <Formula 3>

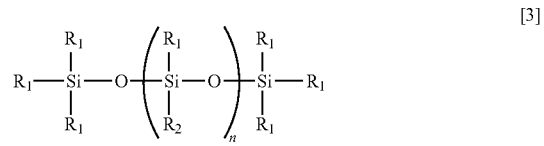

[3]

In the formula, $R_1$ is an optionally substituted alkyl or aryl group, and $R_1$'s may be the same or different. n is an integer of 2 or more. When n=2, $R_2$ is a hydrogen group. When n≥3, $R_2$ is an optionally substituted alkyl group, aryl group, or hydrogen group. At least two or more of $R_2$'s are each a hydrogen group. Combinations of $R_1$ and $R_2$ in a monomer unit may be the same or different for each monomer unit when n≥2.

The molecular structure of the organohydrogen polysiloxane may be a straight-chain, cyclic, branched, or three-dimensional network structure.

In the total amount of the silicone impression material, the content of the SiH groups in the organohydrogen polysiloxanes having at least two SiH groups in a molecule as the component (2) is preferably in the range of 2 to 4 mol based on 1 mol of the alkenyl group in the organopolysiloxanes having at least two unsaturated groups in a molecule as the component (1). When the content of the organohydrogen polysiloxanes having at least two SiH groups in a molecule as the component (2) is less than the lower limit of the above range, the obtained silicone impression material may not be sufficiently cured. When the content of the component (2) is more than the upper limit of the above range, the obtained silicone impression material may be so hard that a large number of cracks may be formed on the surface.

The amount of the organohydrogen polysiloxanes having at least two SiH groups in a molecule as the component (2) is preferably in the range of 3 to 15 wt % based on the total amount of the silicone impression material.

The filler as the component (3) improves the processability of the silicone impression material before being cured or the physical properties of the silicone impression material after being cured. Examples of the component (3) include quartz, cristobalite, diatomaceous earth, fused quartz, glass fiber, titanium dioxide, and fumed silica. The content of the filler as the component (3) is preferably in the range of 20 to 70 wt % based on the total amount of the silicone impression material. When the content of the component (3) is less than the lower limit of the above range, the strength of the cured material may be too low, or separation of oil may be caused. When the content of the component (3) is more than the upper limit of the above range, the viscosity of the silicone impression material before being cured may be so high that the operability and flowability may be degraded.

The filler as the component (3) may be used in conjunction with a pyrolysis method, or a reinforced filler such as precipitated silica and a silica-aluminum mixed oxide, for example. The filler described above may be processed using an organosilane such as hexamethyldisilazane or a siloxane, or processed such that a hydroxyl group is etherified into an alkoxy group, to be hydrophobized. The maximum grain size of the filler is preferably not more than 50 µm. When the maximum grain size of the filler is more than 50 µm, elastic strain may be reduced, permanent strain may be increased, and/or tearing strength may be reduced.

The platinum catalyst as the component (4) is a hydrosilylation catalyst, and promotes a hydrosilylation addition reaction between the alkenyl group in the organopolysiloxanes having at least two unsaturated groups in a molecule as the component (1) and the SiH groups in the organohydrogenpolysiloxanes having at least two SiH groups in a molecule as the component (2). Examples of the platinum catalyst herein include not only platinum catalysts such as platinum black, platinum(II) chloride, a chloroplatinic acid, a reactant between a chloroplatinic acid and a monohydric alcohol, a complex between a chloroplatinic acid and olefines, and platinum bis(acetoacetate), but also platinum-group metal catalysts such as palladium-based catalysts and rhodium-based catalysts. The content of the platinum catalyst is preferably in the range of 0.01 to 0.5 wt % based on the total amount of the silicone impression material.

The sorbitan fatty acid ester based surfactant as the component (a) is a hydrophilizing agent capable of improving the hydrophilicity of the silicone impression material, and is a compound represented by the general formula [4] or [5]:

<Formula 4>

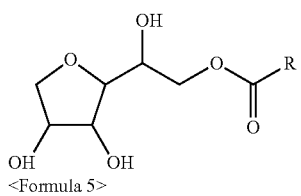

[4]

<Formula 5>

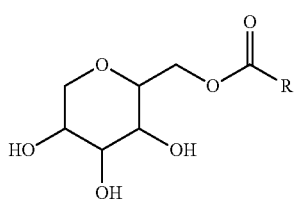

[5]

In the formulas, R represents an unsubstituted or substituted monovalent hydrocarbon group, which may be a straight-chain group, or may be a straight-chain, branched-chain, or cyclic group if there are more than three carbon atoms. R may be any type of substituent that does not hinder a curing reaction.

Examples of the sorbitan fatty acid ester based surfactant as the component (a) include sorbitan monooleate, polyoxyethylene sorbitan oleate, sorbitan laurate, sorbitan caprylate, and polyoxyethylene sorbitan monostearate.

The sorbitan fatty acid ester based surfactant as the component (a) preferably has an HLB in the range of 6.0 to 10.0. When the HLB is less than 6.0, the instantaneous hydrophilicity is low compared to a case where the HLB is in the range of 6.0 to 10.0. When the HLB is more than 10.0, the initial physical properties are not preferable with both permanent strain and elastic strain being slightly too large. The HLB is particularly preferably in the range of 7.0 to 10.0. When the sorbitan fatty acid ester based surfactant as the component (a) has an HLB in this range, a resulting silicone impression material exhibits very high hydrophilicity immediately after water drips, both before and after being cured.

The content of the sorbitan fatty acid ester based surfactant as the component (a) may be in the range of 0.1 to 20 wt %, for example, based on the total amount of the silicone impression material. When the content of the sorbitan fatty acid ester based surfactant as the component (a) is less than the lower limit of the above range, the silicone impression material may not express sufficient hydrophilicity to wet tissues. When the content of the component (a) is more than the upper limit of the above range, the curability and the preservation stability of the silicone impression material may be degraded. The content of the sorbitan fatty acid ester based surfactant as the component (a) is preferably in the range of 0.25 to 6 wt %. When the content of the component (a) is in this range, the silicone impression material is sharply cured, and continuously exhibits high hydrophilicity before and after being cured. When the content of the sorbitan fatty acid ester based surfactant as the component (a) is 0.25 to 5 wt %, in particular, permanent strain may be further reduced, and elastic strain may be further increased. The content of the sorbitan fatty acid ester based surfactant as the component (a) is particularly preferably in the range of 2 to 4 wt %. When the content of the component (a) is in this range, the silicone impression material expresses hydrophilicity immediately after water drips, both before and after being cured, and has small permanent strain, large elastic strain, and good preservation stability.

The nonionic surfactant composed of polyether modified silicone as the component (b) may be represented, for example, by the following structural formula [6]: <Formula 6>

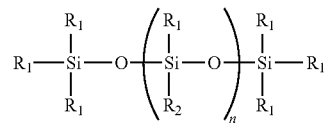

[6]

In the formula, $R_1$ is an optionally substituted alkyl or aryl group, and $R_1$'s may be the same or different. n is an integer of 1 or more. $R_2$ is a substituent having an alkoxy group and composed of a main chain containing an ether bond when n=1; $R_2$ is a substituent having an alkoxy group and composed of a main chain containing an optionally substituted alkyl group, aryl group, or ether bond when n≥2. At least one of $R_2$'s is a substituent having an alkoxy group and composed of a main chain containing an ether bond when n≥2. Combinations of $R_1$ and $R_2$ in a monomer unit may be the same or different for each monomer unit when n≥2. When such a nonionic surfactant composed of polyether modified silicone as the component (b) is used, high hydrophilicity may be maintained compared to a case where different nonionic surfactants composed of polyether modified silicone are used.

The specific structure of $R_2$ may be represented by $RO(C_2H_4O)_n(C_3H_6O)_m$, for example. When $R_2$ has such a structure, high hydrophilicity may be maintained.

The main chain polysiloxane of the polyether modified silicone may be straight or branched, or may be a unit represented by the following structural formula [7]: <Formula 7>

[7]

The structural formula [7] represents a siloxyl unit in which a is 1 or 2, b is 0, 1, or 2, and a+b is 1 to 3. $R_a$ and $R_b$ are an optionally substituted alkyl or aryl group, and may be the same or different. The nonionic surfactant composed of polyether modified silicone as the component (b) preferably has an HLB in the range of 5.0 to 18.0. When the HLB is less than 5.0, the hydrophilicity is low compared to a case where the HLB is in the range of 5.0 to 18.0. The HLB is particularly preferably in the range of 10.0 to 18.0. When the HLB is in the range of 10.0 to 18.0, high hydrophilicity is expressed compared to a case where the HLB is outside the range of 10.0 to 18.0.

The content of the nonionic surfactant composed of polyether modified silicone as the component (b) is preferably 0.25 to 15 wt % based on the total amount of the silicone impression material. When the content of the component (b) is in this range, the silicone impression material is sharply cured, and continuously exhibits high hydrophilicity before and after being cured. The content of the nonionic surfactant composed of polyether modified silicone as the component (b) is particularly preferably in the range of 3 to 10 wt %. When the content of the component (b) is in this range, the silicone impression material expresses high hydrophilicity, and has small permanent strain, large elastic strain, and good preservation stability. When the content of the nonionic surfactant composed of polyether modified silicone as the component (b) is 3 to 7 wt %, in particular, permanent strain may be further reduced, and elastic strain may be further increased.

Examples

Examples of the present invention and comparative examples will be described below. The present invention is not limited to the examples described below. In Examples 1 to 3 and Comparative Examples 1 to 3, a silicone impression material is prepared by kneading catalyst paste (catalyst) and base paste (base) shown in each table with the compounding ratio of 1:1 for the catalyst and base.

Organopolysiloxane compositions, that is, silicone impression materials, according to Example 1 and Comparative Examples 1 to 3 shown in Table 1 were prepared, and the contact angle before being cured, the contact angle after being cured, and the physical properties of the dental impression materials were measured.

The details of the components were as follows.
α-ω Divinyl polysiloxane: DMS-V35, manufactured by Gelest Inc., viscosity: 10 to 110000 mPa·s
Dimethyl hydrogen polysiloxane: HMS-082, manufactured by Gelest Inc., effective hydrogen content: 10 to 58 mol %
Filler 1: FUSELEX X, manufactured by TATSUMORI, average grain size: 3 μm
Filler 2: R812, manufactured by Nippon Aerosil Co., Ltd., specific surface area: 230 to 290 m²/g
Sorbitan fatty acid ester:
  Poem O-80V, manufactured by Riken Vitamin Co., Ltd., HLB: 4.9
  Newcol 80, manufactured by Nippon Nyukazai Co., Ltd., HLB: 6.4
Rikemal L-250A, manufactured by Riken Vitamin Co., Ltd., HLB: 7.4
Rheodol TW-S106V, manufactured by Kao Corporation, HLB: 9.6
Rikemal C-250, manufactured by Riken Vitamin Co., Ltd., HLB: 10.6
Polyoxyalkylene ether: Emulgen 306P, manufactured by Kao Corporation, HLB: 9.4
Polyether modified silicone (side chain type):
  KF-945, manufactured by Shin-Etsu Chemical Co., Ltd., HLB: 4.0
  X-22-4515, manufactured by Shin-Etsu Chemical Co., Ltd., HLB: 5.0
  KF-615A, manufactured by Shin-Etsu Chemical Co., Ltd., HLB: 10.0
  KF-354L, manufactured by Shin-Etsu Chemical Co., Ltd., HLB: 16.0
Polyether modified silicone (terminal type):
  KF-6004, manufactured by Shin-Etsu Chemical Co., Ltd., HLB: 5.0

The contact angle before being cured was measured as follows. The organopolysiloxane composition was poured into a mold with a diameter of 1 mm, carefully not to introduce air bubbles, to form a horizontal top surface. Before the composition was cured, 5 μL of ion exchange water prepared in advance was gently dropped onto the horizontal top surface. The contact angle formed between the water droplet and the composition was measured for 60 seconds since immediately after the water was dropped.

The contact angle after being cured was measured as follows. The organopolysiloxane composition was poured into a mold with a diameter of 1 mm, carefully not to introduce air bubbles, to form a horizontal top surface. Thirty minutes after the composition started being cured, 5 μL of ion exchange water prepared in advance was gently dropped onto the horizontal top surface of the completely cured organopolysiloxane composition. The contact angle formed between the water droplet and the composition was measured for 60 seconds since immediately after the water was dropped.

The working time was measured according to JIS T 6513: 2005, Dental elastomeric impression materials.

The permanent strain was measured according to JIS T 6513:2005, Dental elastomeric impression materials.

The elastic strain was measured according to JIS T 6513: 2005, Dental elastomeric impression materials.

The rubber hardness was measured as follows. A specimen with a certain thickness was fabricated using a glass plate and abridge girder, and the rubber hardness was measured at the center portion of the upper surface of the specimen at 7 minutes and 15 minutes after mixing was started.

The preservation stability was evaluated by measuring the physical properties of the dental impression materials after the compositions according to the example and the comparative examples were left to stand for three months in an environment at 50° C.

TABLE 1

|  | Example 1 | | Comparative Example 1 | | Comparative Example 2 | | Comparative Example 3 | |
| --- | --- | --- | --- | --- | --- | --- | --- | --- |
|  | Catalyst | Base | Catalyst | Base | Catalyst | Base | Catalyst | Base |
| α-ω Divinyl polysiloxane | 61.8 | 40.0 | 61.8 | 40.0 | 61.8 | 46.0 | 61.8 | 44.0 |
| Dimethyl hydrogen polysiloxane | — | 16.0 | — | 16.0 | — | 16.0 | — | 16.0 |

TABLE 1-continued

|  | Example 1 | | Comparative Example 1 | | Comparative Example 2 | | Comparative Example 3 | |
| --- | --- | --- | --- | --- | --- | --- | --- | --- |
|  | Catalyst | Base | Catalyst | Base | Catalyst | Base | Catalyst | Base |
| Filler 1 | 30.0 | 30.0 | 30.0 | 30.0 | 30.0 | 30.0 | 30.0 | 30.0 |
| Filler 2 | 8.0 | 4.0 | 8.0 | 4.0 | 8.0 | 4.0 | 8.0 | 4.0 |
| Platinum catalyst | 0.2 | — | 0.2 | — | 0.2 | — | 0.2 | — |
| Rheodol TW-S106V | — | 4.0 | — | — | — | 4.0 | — | — |
| Emulgen 306P | — | — | — | 4.0 | — | — | — | — |
| KF-354L | — | 6.0 | — | 6.0 | — | — | — | 6.0 |

Figure 2:
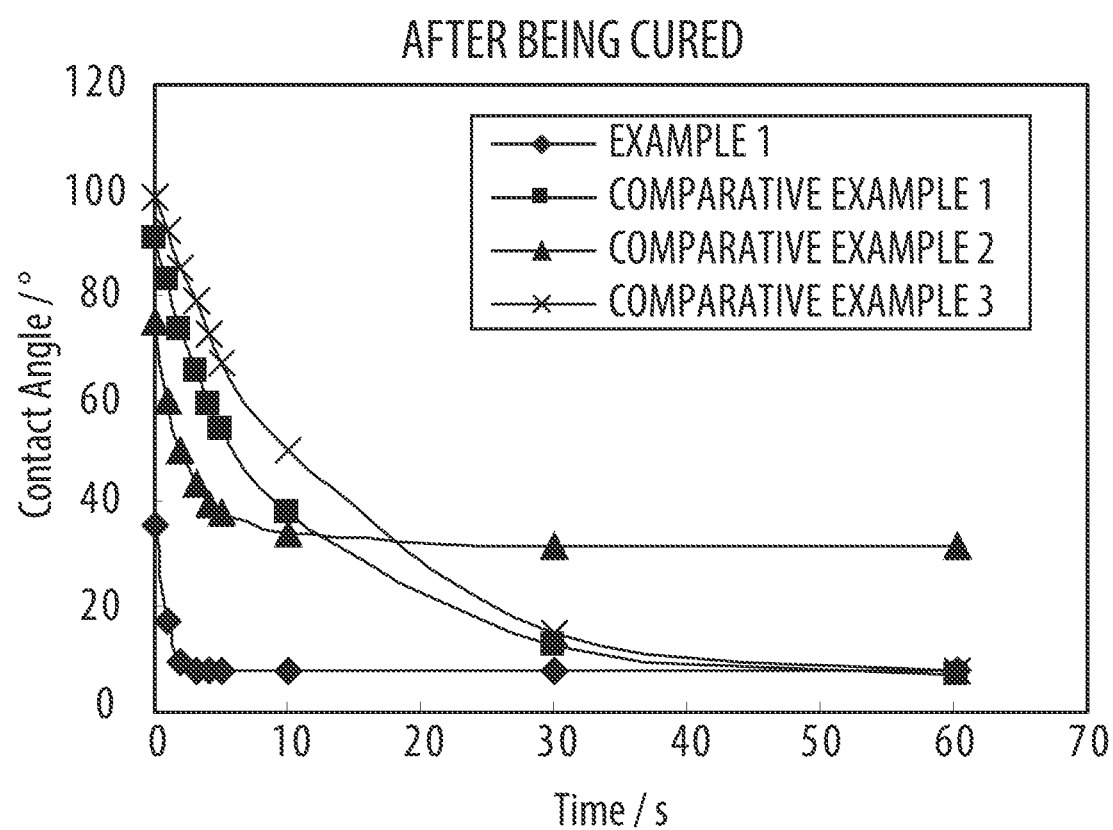
FIG. 2 is a graph showing temporal variations in contact angle of the silicone impression materials according to Example 1 and Comparative Examples 1 to 3 after being cured.

FIGS. 1 and 2 are graphs showing temporal variations in contact angle of the compositions of Example 1 and Comparative Examples 1 to 3 before being cured and after being cured, respectively.

Tables 2 and 3 show the physical properties of the compositions of Example 1 and Comparative Examples 1 to 3 in the initial state and after being left to stand for three months in an environment at 50° C., respectively.

TABLE 2

|  | Example 1 | Comparative Example 1 | Comparative Example 2 | Comparative Example 3 |
| --- | --- | --- | --- | --- |
| Working time/s | 225 | 330 | 225 | 210 |
| Permanent strain/% | 0.3 | 0.9 | 0.3 | 0.3 |
| Elastic strain/% | 5.6 | 6.7 | 5.7 | 5.6 |
| Rubber hardness (after 7 min.) | 34 | 23 | 35 | 36 |
| Rubber hardness (after 15 min.) | 39 | 31 | 37 | 38 |

TABLE 3

|  | Example 1 | Comparative Example 1 | Comparative Example 2 | Comparative Example 3 |
| --- | --- | --- | --- | --- |
| Working time/s | 210 | 645 | 210 | 195 |
| Permanent strain/% | 0.3 | 3.4 | 0.3 | 0.3 |
| Elastic strain/% | 5.7 | 12.8 | 5.7 | 5.7 |
| Rubber hardness (after 7 min.) | 34 | 5 | 34 | 35 |
| Rubber hardness (after 15 min.) | 38 | 18 | 38 | 39 |

The composition of Example 1 expressed hydrophilicity immediately after water dripped, both before and after being cured, and continuously exhibited high hydrophilicity thereafter. The initial physical properties of the composition of Example 1 were desirable with small permanent strain and large elastic strain. The composition was sharply cured, and had good preservation stability.

The composition of Comparative Example 1 gradually expressed hydrophilicity in the course of time after water dripped, and achieved a contact angle comparable to that achieved in Example 1 in 60 seconds after being cured, but had a contact angle larger than that achieved in Example 1 before being cured. The composition of Comparative Example 1 did not maintain desirable initial physical properties and good preservation stability.

The composition of Comparative Example 2 expressed hydrophilicity more immediately than in Comparative Example 1, both before and after being cured. However, the composition did not express instantaneous hydrophilicity comparable to that achieved in Example 1, and did not achieve a sufficiently small contact angle in 60 seconds after being cured. The composition of Comparative Example 2 maintained desirable initial physical properties and good preservation stability.

The composition according of Comparative Example 3 gradually expressed hydrophilicity in the course of time after water dripped, and achieved a contact angle comparable to that achieved in Example 1 in 60 seconds after being cured, but had a contact angle larger than that achieved in Example 1 before being cured. The composition of Comparative Example 3 maintained desirable initial physical properties and good preservation stability.

Organopolysiloxane compositions of Examples 2 to 5 shown in Table 4 were prepared, and the contact angle before being cured, the contact angle after being cured, and the physical properties of the dental impression materials were measured. In Examples 2 to 5 shown in Table 4, the contents of Rheodol TW-S106V serving as the sorbitan fatty acid ester and the polyether modified silicone were changed from those in the composition of Example 1.

TABLE 4

|  | Example 2 | | Example 3 | | Example 4 | | Example 5 | |
| --- | --- | --- | --- | --- | --- | --- | --- | --- |
|  | Catalyst | Base | Catalyst | Base | Catalyst | Base | Catalyst | Base |
| α-ω Divinyl polysiloxane | 61.8 | 46.0 | 61.8 | 28.0 | 61.8 | 49.0 | 61.8 | 14.0 |
| Dimethyl hydrogen polysiloxane | — | 16.0 | — | 16.0 | — | 16.0 | — | 16.0 |
| Filler 1 | 30.0 | 30.0 | 30.0 | 30.0 | 30.0 | 30.0 | 30.0 | 30.0 |
| Filler 2 | 8.0 | 4.0 | 8.0 | 4.0 | 8.0 | 4.0 | 8.0 | 4.0 |
| Platinum catalyst | 0.2 | — | 0.2 | — | 0.2 | — | 0.2 | — |
| Rheodol TW-S106V | — | 2.0 | — | 8.0 | — | 0.5 | — | 12.0 |
| KF-354L | — | 2.0 | — | 14.0 | — | 0.5 | — | 24.0 |

Figure 3:
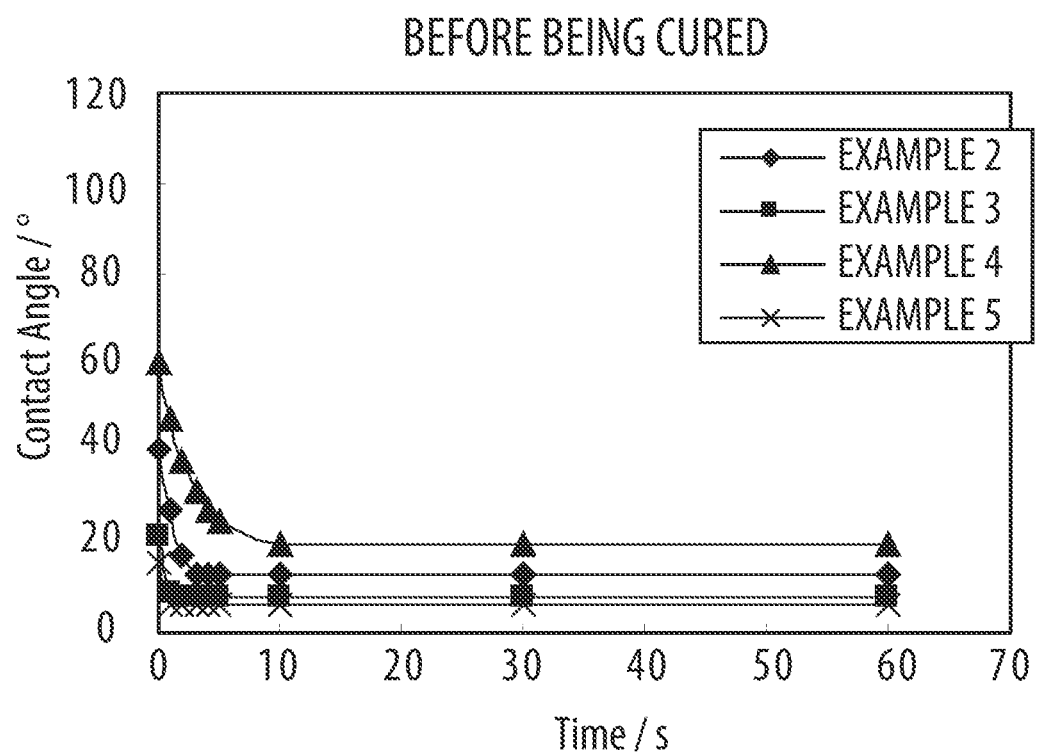
FIG. 3 is a graph showing temporal variations in contact angle of silicone impression materials according to Examples 2 to 5 before being cured.
Figure 4:
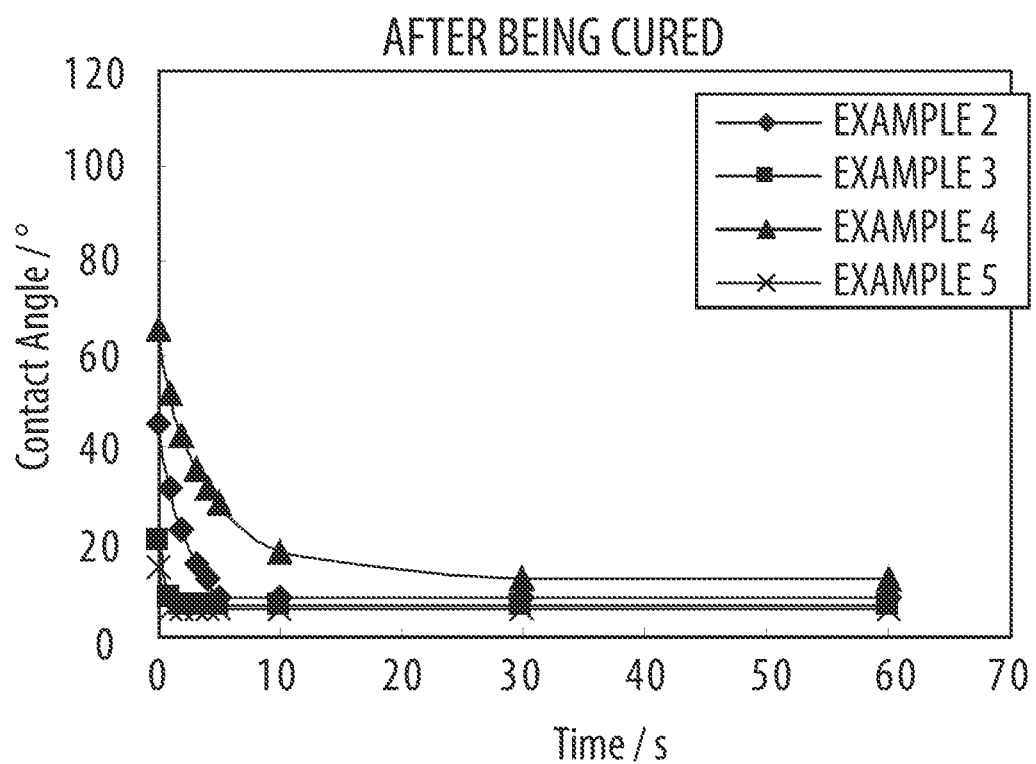
FIG. 4 is a graph showing temporal variations in contact angle of the silicone impression materials according to Examples 2 to 5 after being cured.

FIGS. 3 and 4 are graphs showing temporal variations in contact angle of the compositions of Examples 2 to 5 before being cured and after being cured, respectively.

Tables 5 and 6 show the physical properties of the compositions of Examples 2 to 5 in the initial state and after being left to stand for three months in an environment at 50° C., respectively.

TABLE 5

|  | Example 2 | Example 3 | Example 4 | Example 5 |
| --- | --- | --- | --- | --- |
| Working time/s | 195 | 210 | 225 | 255 |
| Permanent strain/% | 0.3 | 0.3 | 0.3 | 0.6 |
| Elastic strain/% | 5.6 | 5.6 | 5.7 | 6.1 |
| Rubber hardness (after 7 min.) | 34 | 33 | 35 | 30 |
| Rubber hardness (after 15 min.) | 38 | 38 | 38 | 38 |

TABLE 6

|  | Example 2 | Example 3 | Example 4 | Example 5 |
|---|---|---|---|---|
| Working time/s | 210 | 210 | 225 | 345 |
| Permanent strain/% | 0.3 | 0.3 | 0.3 | 1.2 |
| Elastic strain/% | 5.6 | 5.7 | 5.6 | 6.9 |
| Rubber hardness (after 7 min.) | 34 | 34 | 33 | 23 |
| Rubber hardness (after 15 min.) | 39 | 38 | 39 | 34 |

The composition of Example 2 exhibited hydrophilicity lower than that in Example 1, but expressed instantaneous hydrophilicity higher than that in Comparative Example 2, both before and after being cured. The initial physical properties of the composition of Example 2 were desirable with small permanent strain and large elastic strain. The composition was sharply cured, and had good preservation stability.

The composition of Example 3 expressed hydrophilicity immediately after water dripped, both before and after being cured, and continuously exhibited high hydrophilicity thereafter. The initial physical properties of the composition of Example 3 were desirable with small permanent strain and large elastic strain. The composition was sharply cured, and had good preservation stability.

The composition of Example 4 exhibited hydrophilicity slightly lower than that in Example 2. The initial physical properties of the composition of Example 4 were desirable with small permanent strain and large elastic strain. The composition was sharply cured, and had good preservation stability.

The composition of Example 5 expressed hydrophilicity immediately after water dripped, both before and after being cured, and continuously exhibited high hydrophilicity thereafter. For the initial physical properties, the composition of Example 5 exhibited slightly large permanent strain and slightly large elastic strain.

Organopolysiloxane compositions of Examples 6 to 9 shown in Table 7 were prepared, and the contact angle before being cured, the contact angle after being cured, and the physical properties of the dental impression materials were measured. In Examples 6 to 9 shown in Table 7, the type of the sorbitan fatty acid ester was changed from that in the composition of Example 1.

TABLE 7

|  | Example 6 | | Example 7 | | Example 8 | | Example 9 | |
|---|---|---|---|---|---|---|---|---|
|  | Catalyst | Base | Catalyst | Base | Catalyst | Base | Catalyst | Base |
| α-ω Divinyl polysiloxane | 61.8 | 40.0 | 61.8 | 40.0 | 61.8 | 40.0 | 61.8 | 40.0 |
| Dimethyl hydrogen polysiloxane | — | 16.0 | — | 16.0 | — | 16.0 | — | 16.0 |
| Filler 1 | 30.0 | 30.0 | 30.0 | 30.0 | 30.0 | 30.0 | 30.0 | 30.0 |
| Filler 2 | 8.0 | 4.0 | 8.0 | 4.0 | 8.0 | 4.0 | 8.0 | 4.0 |
| Platinum catalyst | 0.2 | — | 0.2 | — | 0.2 | — | 0.2 | — |
| PoemO-80V | — | 4.0 | — | — | — | — | — | — |
| Newcol 80 | — | — | — | 4.0 | — | — | — | — |
| Rikemal L-250A | — | — | — | — | — | 4.0 | — | — |
| Rikemal C-250 | — | — | — | — | — | — | — | 4.0 |
| KF-354L | — | 6.0 | — | 6.0 | — | 6.0 | — | 6.0 |

Figure 5:
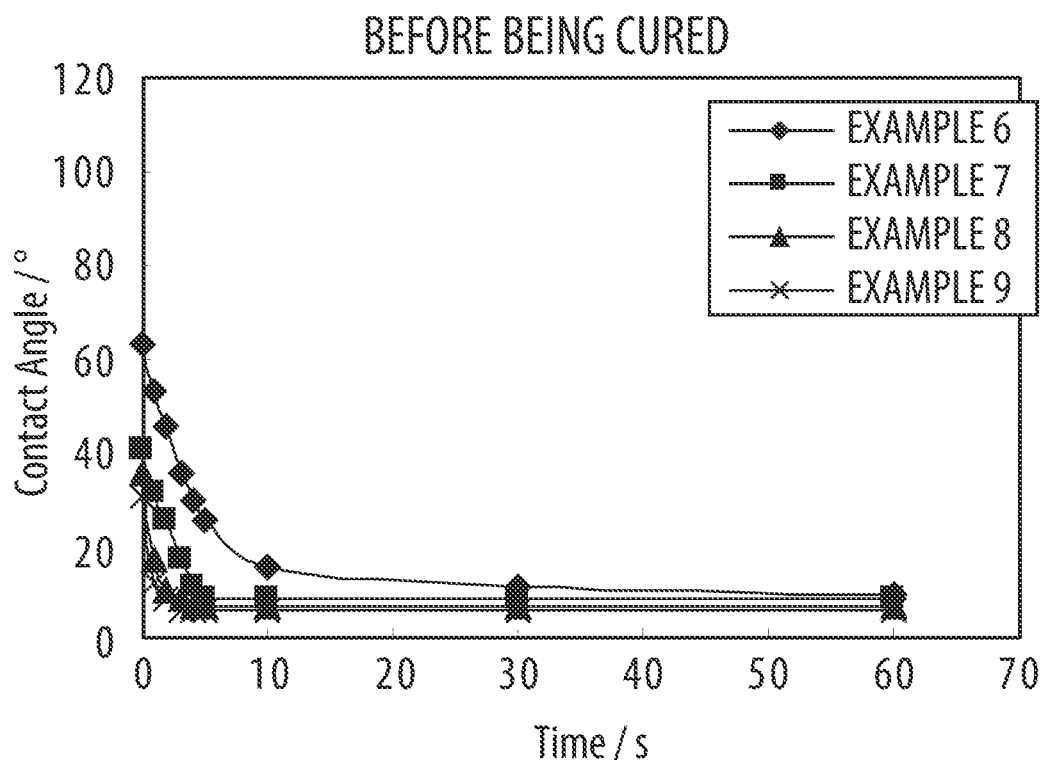
FIG. 5 is a graph showing temporal variations in contact angle of silicone impression materials according to Examples 6 to 9 before being cured.
Figure 6:
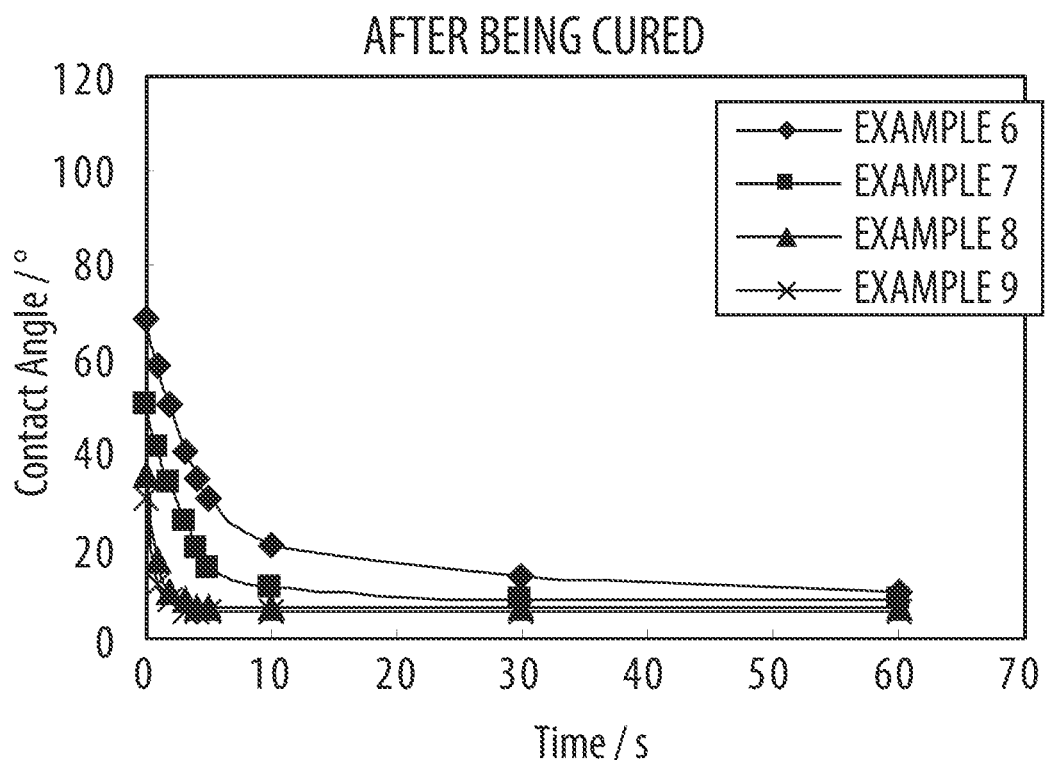
FIG. 6 is a graph showing temporal variations in contact angle of the silicone impression materials according to Examples 6 to 9 after being cured.

FIGS. 5 and 6 are graphs showing temporal variations in contact angle of the compositions of Examples 6 to 9 before being cured and after being cured, respectively.

Tables 8 and 9 show the physical properties of the compositions of Examples 6 to 9 in the initial state and after being left to stand for three months in an environment at 50° C., respectively.

TABLE 8

|  | Example 6 | Example 7 | Example 8 | Example 9 |
|---|---|---|---|---|
| Working time/s | 225 | 210 | 225 | 255 |
| Permanent strain/% | 0.3 | 0.3 | 0.3 | 0.4 |
| Elastic strain/% | 5.6 | 5.7 | 5.6 | 5.9 |
| Rubber hardness (after 7 min.) | 34 | 33 | 34 | 29 |
| Rubber hardness (after 15 min.) | 39 | 37 | 38 | 38 |

TABLE 9

|  | Example 6 | Example 7 | Example 8 | Example 9 |
|---|---|---|---|---|
| Working time/s | 210 | 210 | 225 | 315 |
| Permanent strain/% | 0.3 | 0.3 | 0.3 | 0.9 |
| Elastic strain/% | 5.5 | 5.6 | 5.7 | 6.3 |
| Rubber hardness (after 7 min.) | 33 | 34 | 33 | 27 |
| Rubber hardness (after 15 min.) | 39 | 39 | 37 | 34 |

Among the compositions of Examples 6 to 8, the composition of Example 8 exhibited the highest hydrophilicity, and the composition of Example 6 exhibited the lowest hydrophilicity, which was still sufficiently higher than the hydrophilicities achieved in the comparative examples. The compositions of Examples 6 to 8 expressed hydrophilicity immediately after water drips, both before and after being cured, and continuously exhibited high hydrophilicity thereafter. The initial physical properties of the compositions of Examples 6 to 8 were desirable with small permanent strain and large elastic strain. The compositions were sharply cured, and had good preservation stability.

The composition of Example 9 expressed hydrophilicity immediately after water dripped, both before and after being cured, and continuously exhibited high hydrophilicity thereafter. For the initial physical properties, the composition of Example 9 exhibited slightly large permanent strain and slightly large elastic strain.

An organopolysiloxane composition of Example 10 shown in Table 10 was prepared, and the contact angle before being cured, the contact angle after being cured, and the physical properties of the dental impression material were measured. In Example 10 shown in Table 10, the polyether modified silicone was changed to a terminal type in contrast to the composition of Example 1.

TABLE 10

|  | Example 10 | |
| --- | --- | --- |
|  | Catalyst | Base |
| α-ω Divinyl polysiloxane | 61.8 | 40.0 |
| Dimethyl hydrogen polysiloxane | — | 16.0 |
| Filler 1 | 30.0 | 30.0 |
| Filler 2 | 8.0 | 4.0 |
| Platinum catalyst | 0.2 | — |
| Rheodol TW-S106V | — | 4.0 |
| KF-6004 | — | 6.0 |

Figure 7:
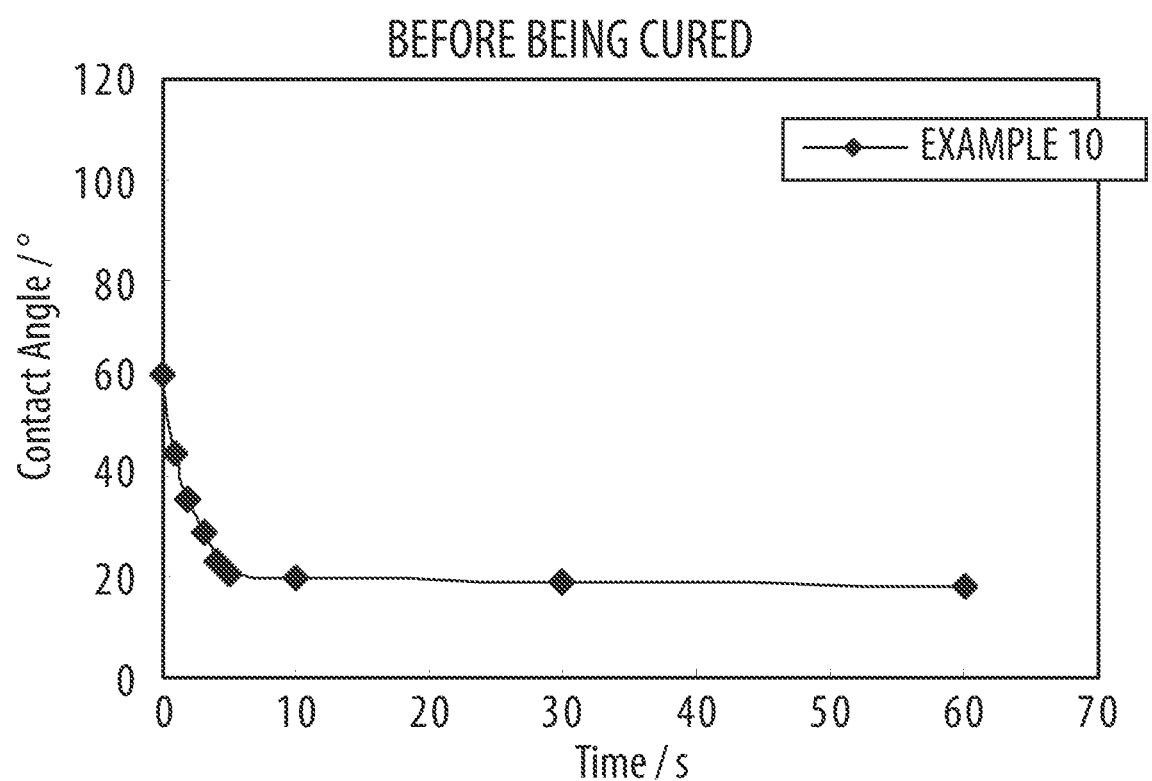
FIG. 7 is a graph showing temporal variations in contact angle of a silicone impression material according to Example 10 before being cured.
Figure 8:
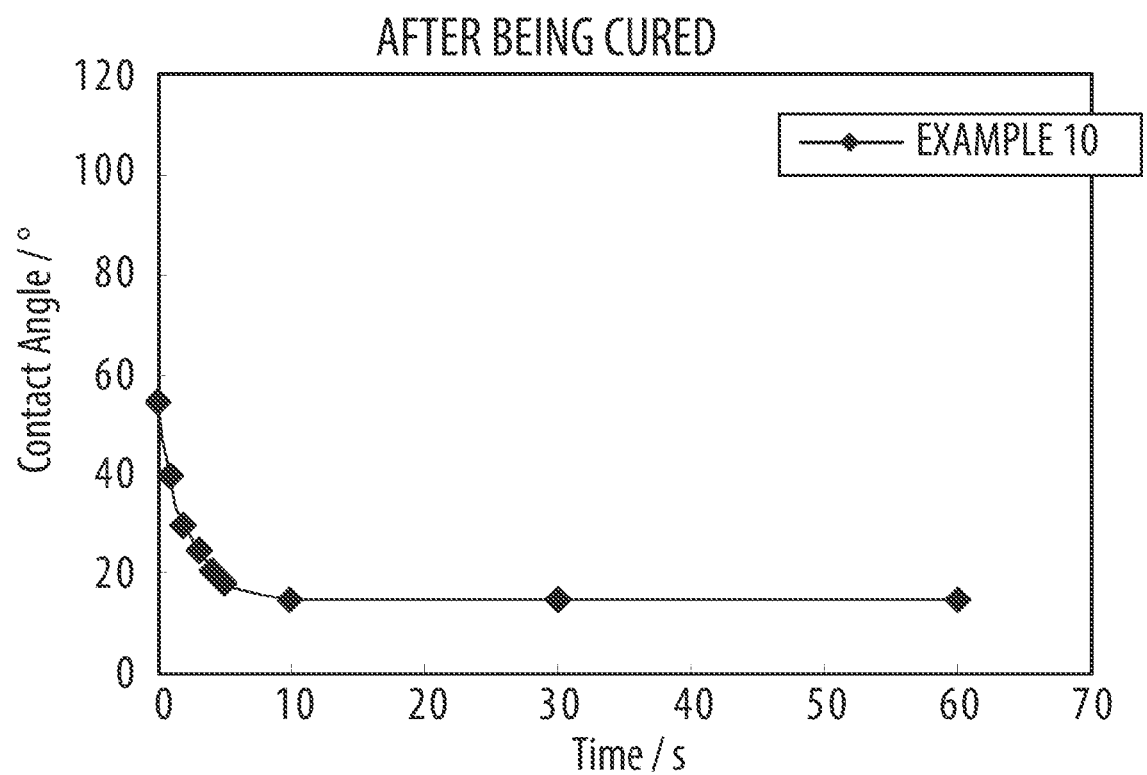
FIG. 8 is a graph showing temporal variations in contact angle of the silicone impression material according to Example 10 after being cured.

FIGS. 7 and 8 are graphs showing temporal variations in contact angle of the composition of Example 10 before being cured and after being cured, respectively.

Tables 11 and 12 show the physical properties of the composition of Example 10 in the initial state and after being left to stand for three months in an environment at 50° C., respectively.

TABLE 11

|  | Example 10 |
| --- | --- |
| Working time/s | 225 |
| Permanent strain/% | 0.3 |
| Elastic strain/% | 5.7 |
| Rubber hardness (after 7 min.) | 32 |
| Rubber hardness (after 15 min.) | 37 |

TABLE 12

|  | Example 10 |
| --- | --- |
| Working time/s | 225 |
| Permanent strain/% | 0.3 |
| Elastic strain/% | 5.6 |
| Rubber hardness (after 7 min.) | 33 |
| Rubber hardness (after 15 min.) | 38 |

The composition of Example 10 expressed hydrophilicity immediately after water dripped, both before and after being cured. However, the hydrophilicity expressed by the composition of Example 10 in 60 seconds after being cured was not as high as that in Example 1. The initial physical properties of the composition of Example 10 were desirable with small permanent strain and large elastic strain. The composition was sharply cured, and had good preservation stability.

Organopolysiloxane compositions of Examples 11 to 13 shown in Table 13 were prepared, and the contact angle before being cured, the contact angle after being cured, and the physical properties of the dental impression materials were measured. In Examples 11 to 13 shown in Table 13, the type of the polyether modified silicone was changed in contrast to the composition of Example 1.

TABLE 13

|  | Example 11 | | Example 12 | | Example 13 | |
| --- | --- | --- | --- | --- | --- | --- |
|  | Catalyst | Base | Catalyst | Base | Catalyst | Base |
| α-ω Divinyl polysiloxane | 61.8 | 40.0 | 61.8 | 40.0 | 61.8 | 40.0 |
| Dimethyl hydrogen polysiloxane | — | 16.0 | — | 16.0 | — | 16.0 |
| Filler 1 | 30.0 | 30.0 | 30.0 | 30.0 | 30.0 | 30.0 |
| Filler 2 | 8.0 | 4.0 | 8.0 | 4.0 | 8.0 | 4.0 |
| Platinum catalyst | 0.2 | — | 0.2 | — | 0.2 | — |
| Rheodol TW-S106V | — | 4.0 | — | 4.0 | — | 4.0 |
| KF-945 | — | 6.0 | — | — | — | — |
| X-22-4515 | — | — | — | 6.0 | — | — |
| KF-615A | — | — | — | — | — | 6.0 |

Figure 9:
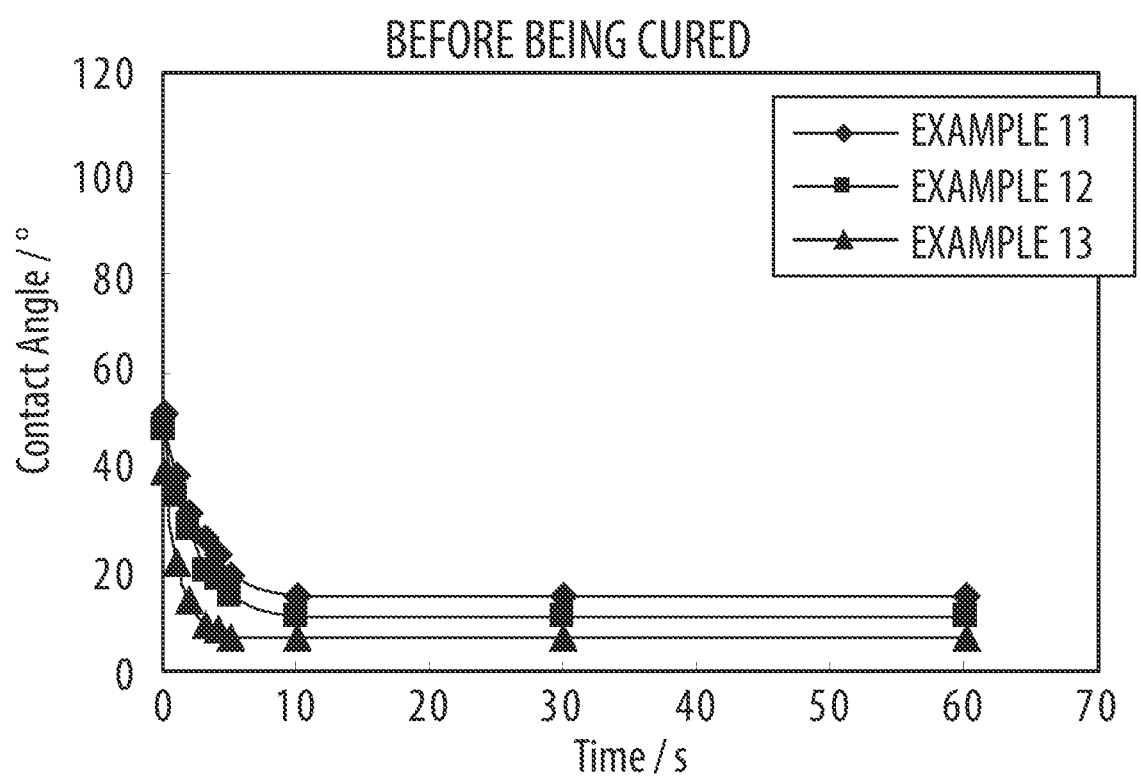
FIG. 9 is a graph showing temporal variations in contact angle of silicone impression materials according to Examples 11 to 13 before being cured.

FIGS. 9 and 10 are graphs showing temporal variations in contact angle of the compositions of Examples 11 to 13 before being cured and after being cured, respectively.

Tables 14 and 15 show the physical properties of the compositions of Examples 11 to 13 in the initial state and after being left to stand for three months in an environment at 50° C., respectively.

TABLE 14

|  | Example 11 | Example 12 | Example 13 |
| --- | --- | --- | --- |
| Working time/s | 195 | 225 | 210 |
| Permanent strain/% | 0.3 | 0.3 | 0.3 |
| Elastic strain/% | 5.6 | 5.8 | 5.6 |
| Rubber hardness (after 7 min.) | 33 | 34 | 35 |
| Rubber hardness (after 15 min.) | 39 | 38 | 38 |

TABLE 15

|  | Example 11 | Example 12 | Example 13 |
| --- | --- | --- | --- |
| Working time/s | 210 | 225 | 195 |
| Permanent strain/% | 0.3 | 0.3 | 0.3 |
| Elastic strain/% | 5.7 | 5.7 | 5.6 |
| Rubber hardness (after 7 min.) | 34 | 34 | 33 |
| Rubber hardness (after 15 min.) | 37 | 39 | 37 |

Among the compositions of Examples 11 to 13, the composition of Example 13 exhibited the highest hydrophilicity, and the composition of Example 11 exhibited the lowest hydrophilicity, which was still sufficiently higher than the hydrophilicities achieved in the comparative examples. The compositions of Examples 11 to 13 expressed hydrophilicity immediately after water drips, both before and after being cured, and continuously exhibited high hydrophilicity thereafter. The initial physical properties of the compositions of Examples 11 to 13 were desirable with small permanent strain and large elastic strain. The compositions were sharply cured, and had good preservation stability.

As has been described above, the silicone impression material according to the present invention exhibited hydrophilicity immediately after being pressed in the oral cavity, and had sufficiently small hydrophilicity values, thus providing good hydrophilicity in actual impression sampling. In addition, the silicone impression material according to the present invention exhibited desirable physical properties for a dental impression material, and had good preservation stability.

Although not specifically stated in the claims, additional compositions according to the present invention are listed below.

(i) A silicone impression material having high hydrophilicity, in which the sorbitan fatty acid ester based surfactant as the component (a) has an HLB of 7 to 10.0.
(ii) A silicone impression material having high hydrophilicity, in which the sorbitan fatty acid ester based surfactant as the component (a) accounts for 2 to 4 wt %.
(iii) A silicone impression material having high hydrophilicity, in which the polyether modified silicone as the component (b) has an HLB of 10.0 to 18.0.
(iv) A silicone impression material having high hydrophilicity, in which the nonionic surfactant composed of polyether modified silicone as the component (b) accounts for 3 to 7 wt %.
(v) A silicone impression material having high hydrophilicity, in which the filler as the component (3) has a maximum grain size of not more than 50 μm.
(vi) A silicone impression material having high hydrophilicity, in which a content ratio of the sorbitan fatty acid ester based surfactant as the component (a) and the nonionic surfactant composed of polyether modified silicone as the component (b) is 1:1.5 to 1:1.8.
(vii) A silicone impression material having high hydrophilicity, in which:
  the organopolysiloxanes having at least two unsaturated groups in a molecule as the component (1) account for 37.9 to 50.9 wt %;
  the organohydrogen polysiloxanes having at least two SiH groups in a molecule as the component (2) account for 8 wt %;
  the filler as the component (3) accounts for 36 wt %;
  the platinum catalyst as the component (4) accounts for 0.1 wt %;
  the sorbitan fatty acid ester based surfactant as the component (a) accounts for 0.25 to 5 wt %; and
  the nonionic surfactant composed of polyether modified silicone as the component (b) accounts for 0.25 to 12 wt %.
(viii) A silicone impression material having high hydrophilicity according to (vii) above, in which:
  the organopolysiloxanes having at least two unsaturated groups in a molecule as the component (1) are α-ω divinyl polysiloxane;
  the organohydrogen polysiloxanes having at least two SiH groups in a molecule as the component (2) are dimethyl hydrogen polysiloxane;
  the sorbitan fatty acid ester based surfactant as the component (a) is sorbitan monooleate, polyoxyethylene sorbitan oleate, sorbitan laurate, sorbitan caprylate, or polyoxyethylene sorbitan monostearate; and
  the nonionic surfactant composed of polyether modified silicone as the component (b) is a side chain type or a terminal type.
(ix) A silicone impression material having high hydrophilicity, in which:
  the organopolysiloxanes having at least two unsaturated groups in a molecule as the component (1) account for 44.9 to 50.9 wt %;
  the organohydrogen polysiloxanes having at least two SiH groups in a molecule as the component (2) account for 8 wt %;
  the filler as the component (3) accounts for 36 wt %;
  the platinum catalyst as the component (4) accounts for 0.1 wt %;
  the sorbitan fatty acid ester based surfactant as the component (a) accounts for 2 to 4 wt %; and
  the nonionic surfactant composed of polyether modified silicone as the component (b) accounts for 3 to 7 wt %.
(x) A silicone impression material having high hydrophilicity according to (ix) above, in which:
  the organopolysiloxanes having at least two unsaturated groups in a molecule as the component (1) are α-ω divinyl polysiloxane;
  the organohydrogen polysiloxanes having at least two SiH groups in a molecule as the component (2) are dimethyl hydrogen polysiloxane;
  the sorbitan fatty acid ester based surfactant as the component (a) is polyoxyethylene sorbitan monostearate or sorbitan laurate; and
  the nonionic surfactant composed of polyether modified silicone as the component (b) is a side chain type.

In the present invention, a sorbitan fatty acid ester based surfactant and a nonionic surfactant composed of polyether modified silicone are used in combination as a hydrophilizing agent not containing a siloxane polymer and a hydrophilizing agent containing a siloxane polymer, respectively. Thus, it is possible to provide a silicone impression material that exhibits instantaneous hydrophilicity before being cured, that exhibits high hydrophilicity after being cured, that has preferable properties for a dental impression material, and that has good preservation stability.

While certain features of the invention have been described with reference to example embodiments, the description is not intended to be construed in a limiting sense. Various modifications of the example embodiments, as well as other embodiments of the invention, which are apparent to persons skilled in the art to which the invention pertains, are deemed to lie within the spirit and scope of the invention.

The invention claimed is:

1. A silicone impression material comprising, by the total weigh of the material:
  20% to 70% organopolysiloxanes having at least two unsaturated groups in a molecule;
  3% to 15% organohydrogen polysiloxanes having at least two SiH groups in a molecule;
  20% to 70% of a filler;
  0.01 to 0.5% of a platinum catalyst;
  0.25% to 6% of a sorbitan fatty acid ester based surfactant having an HLB of 6.0 to 10.0 as a hydrophilizing agent; and
  0.25% to 15% of a nonionic surfactant, as a hydrophilizing agent, composed of a polyether modified silicone;
  wherein the material, both in an uncured state and in a cured state, is capable of achieving a contact angle measured between a droplet of ion exchange water and the material measured 10 seconds after the droplet of ion exchange water is dropped onto a surface of the material that is smaller than a contact angle that can be achieved under identical conditions by a composition that is identical to the material except that the composition does not contain the sorbitan fatty acid ester based surfactant.

2. The silicone impression material according to claim 1, wherein the nonionic surfactant is a compound of formula [1]:

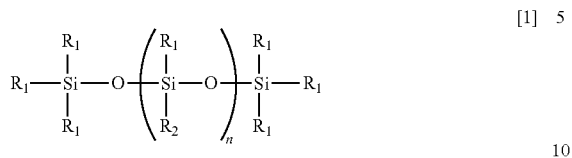

wherein $R_1$ is an alkyl or aryl group; $R_1$'s are the same or different; n is an integer of 1 or more; $R_2$ is a substituent having an alkoxy group and composed of a main chain containing an ether bond when n=1; $R_2$ is a substituent having an alkoxy group and composed of a main chain containing an optionally substituted alkyl group, aryl group, or ether bond when n≥2; at least one of $R_2$'s is a substituent having an alkoxy group and composed of a main chain containing an ether bond when n≥2; and combinations of $R_1$ and $R_2$ in a monomer unit are the same or different for each monomer unit when n≥2.

3. The silicone impression material according to claim 1, wherein the polyether modified silicone has an HLB of 5.0 to 18.0.

4. The silicone impression material according to claim 1, wherein a content ratio of the sorbitan fatty acid ester based surfactant and the nonionic surfactant is 1:1 to 1:2.

* * * * *